US010039597B2

(12) United States Patent
Mujwid

(10) Patent No.: US 10,039,597 B2
(45) Date of Patent: Aug. 7, 2018

(54) SURGICAL CUTTING INSTRUMENT AND RELATED METHODS

(71) Applicant: Boston Scientific Scimed, Inc., Maple Grove, MN (US)

(72) Inventor: James R. Mujwid, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 456 days.

(21) Appl. No.: 13/664,915

(22) Filed: Oct. 31, 2012

(65) Prior Publication Data

US 2013/0110126 A1    May 2, 2013

Related U.S. Application Data

(60) Provisional application No. 61/553,476, filed on Oct. 31, 2011.

(51) Int. Cl.
*A61B 17/32* (2006.01)
*A61B 18/14* (2006.01)
(Continued)

(52) U.S. Cl.
CPC ...... *A61B 18/148* (2013.01); *A61B 17/32056* (2013.01); *A61B 17/42* (2013.01); *A61B 2017/4216* (2013.01); *A61B 2018/00547* (2013.01); *A61B 2018/00559* (2013.01); *A61B 2018/00565* (2013.01); *A61B 2018/00595* (2013.01); *A61B 2018/00601* (2013.01); *A61B 2018/00982* (2013.01); *A61B 2018/142* (2013.01); *A61B 2018/144* (2013.01); *A61B 2018/1407* (2013.01)

(58) Field of Classification Search
CPC .......... A61B 10/0266; A61B 17/32056; A61B 17/42; A61B 18/148; A61B 2018/142; A61B 2018/00982; A61B 2018/00601; A61B 2018/00595; A61B 2018/00565; A61B 2018/00559; A61B 2018/00547; A61B 2018/144; A61B 2018/1407; A61B 2017/4216
USPC ....................................................... 606/167
See application file for complete search history.

(56) References Cited

U.S. PATENT DOCUMENTS

| | | | |
|---|---|---|---|
| 2,738,790 A | 3/1956 | Todt et al. | |
| 3,580,313 A | 5/1971 | McKnight | |

(Continued)

FOREIGN PATENT DOCUMENTS

| | | |
|---|---|---|
| CN | 101027012 A | 8/2007 |
| CN | 101500507 A | 8/2009 |

(Continued)

OTHER PUBLICATIONS

Office Action for Chinese Application No. 201510993909.6, dated Aug. 24, 2017, 6 pages.

(Continued)

*Primary Examiner* — Richard Louis
(74) *Attorney, Agent, or Firm* — Brake Hughes Bellermann LLP

(57) ABSTRACT

Described are surgical cutting tools and related methods, useful to sever tissue, optionally cauterizing the tissue; the cutting tool includes a frame that can be extended and retracted at the distal end of the cutting tool such that the frame supports a cutting element useful to cut tissue.

21 Claims, 8 Drawing Sheets

(51) Int. Cl.
*A61B 17/42* (2006.01)
*A61B 17/3205* (2006.01)
*A61B 18/00* (2006.01)

(56) References Cited

U.S. PATENT DOCUMENTS

| | | | |
|---|---|---|---|
| 3,763,860 A | 10/1973 | Clarke | |
| 3,858,783 A | 1/1975 | Kapitanov et al. | |
| 3,910,279 A * | 10/1975 | Okada | A61B 18/14 606/47 |
| 3,995,619 A | 12/1976 | Glatzer | |
| 4,172,458 A | 10/1979 | Pereyra | |
| 4,181,131 A * | 1/1980 | Ogiu | A61B 18/14 606/47 |
| 4,235,238 A | 11/1980 | Ogiu et al. | |
| 4,246,660 A | 1/1981 | Wevers | |
| 4,441,497 A | 4/1984 | Paudler | |
| 4,509,516 A | 4/1985 | Richmond | |
| 5,149,329 A | 9/1992 | Richardson | |
| 5,188,636 A | 2/1993 | Fedotov | |
| 5,254,106 A | 10/1993 | Feaster et al. | |
| 5,281,237 A | 1/1994 | Gimpelson | |
| 5,520,700 A | 5/1996 | Beyar et al. | |
| 5,520,703 A | 5/1996 | Essig | |
| 5,944,732 A | 8/1999 | Raulerson et al. | |
| 6,099,538 A | 8/2000 | Moses | |
| 6,099,551 A | 8/2000 | Gabbay | |
| 6,168,611 B1 | 1/2001 | Risvi | |
| 7,037,255 B2 | 5/2006 | Inman | |
| 7,048,682 B2 | 5/2006 | Neisz et al. | |
| 7,131,943 B2 | 11/2006 | Kammerer | |
| 7,371,245 B2 | 5/2008 | Evans et al. | |
| 2003/0163129 A1* | 8/2003 | Lee | A61B 8/0825 606/47 |
| 2008/0207988 A1 | 8/2008 | Hanes | |
| 2013/0018402 A1* | 1/2013 | Polo | A61B 17/32056 606/170 |

FOREIGN PATENT DOCUMENTS

| | | |
|---|---|---|
| DE | 2305815 DE | 2/1973 |
| DE | 4220283 C2 | 5/1994 |
| SU | 1225547 A1 | 4/1986 |
| SU | 1342486 A | 10/1987 |
| WO | WO9730638 A1 | 8/1997 |
| WO | WO9835606 A1 | 8/1998 |
| WO | WO0074633 A2 | 12/2000 |
| WO | 2007149348 A2 | 12/2007 |

OTHER PUBLICATIONS

First Office Action for Chinese Application No. 201510993909.6, dated Feb. 3, 2017, 14 pages.

* cited by examiner

SURGICAL CUTTING INSTRUMENT AND RELATED METHODS

PRIORITY CLAIM

The present non-provisional patent Application claims priority under 35 USC § 119(e) from U.S. Provisional Patent Application having Ser. No. 61/533,476, filed Oct. 31, 2011, entitled "LAPAROSCOPIC ELECTROSURGICAL DISSECTION TOOL WITH SHAPE MEMORY TIP," the entirety of which is incorporated herein by reference.

FIELD OF THE INVENTION

The following describes surgical instruments useful for cutting anatomical tissue in laparoscopic and other type of surgeries, and related methods, wherein the instruments include a cutting element supported by a retractable frame.

BACKGROUND

Surgical cutting instruments are useful for a variety of surgical procedures designed to remove or repair healthy or diseased tissue. The tissue may be soft tissue such as muscle, or the tissue may be bone. Certain specific procedures are useful to remove polyps, a uterus (hysterectomies), cancer, tonsils, fibroids, and the like. If tissue is vascularized, the cutting instrument may also cauterize the tissue to reduce bleeding.

One procedure for removing tissue is a "hysterectomy," which removes reproductive organs of a female, particularly the uterus. A typical hysterectomy can be performed using an open abdominal process, which provides open access and clear view of the organs in question. However, an open abdominal incision increases the risk of injury and infection. As an alternative, the vaginal canal can be used to reach the uterus, but removing the uterus through the vagina requires also removing the cervix which is not always desirable. It is generally preferred that as little tissue as possible be removed and it is understood that where possible it is best to not disturb the cervix.

At present, laparoscopic methods can be preferred for a hysterectomy, based on improved safety, brevity, reduced recovery time, reduced blood loss, and reduced risk of complications. A laparoscopic hysterectomy can require only very tiny incisions in the abdomen. Among various versions of laparoscopic hysterectomy procedures are those in which an electrical cutting knife and cauterizing tool is used to separate tissue and organs from where they are attached.

For cutting and cauterizing tissue, uterus tissue or otherwise, an electrode-tipped surgical instrument can be used. In a hysterectomy in particular, electrode-tipped instruments have been used to cut the uterus from the cervix at the uterine isthmus, which is the inferior-posterior part of uterus on the cervical end of the uterus, a location at which the uterine muscle is narrower and thinner. In some cases, ovaries are cut away from their attachment to the uterus, e.g., at the fallopian tubes, and are left within the patient while the uterus is removed. Alternately, a surgeon may desire to keep the ovaries with the uterus, separate the ovaries from their attachment to the body, and remove the ovaries with the uterus.

To separate tissue for removal, a surgeon can use a tip of an electrical knife to apply electrical current to the region of tissue where resection is desired. In various conventional surgical cutting instruments, an electrical knife can be arranged as a monopolar system having a single electrode at the instrument tip. A patient's body or bulk tissue forms an electrically conductive path to a second electrode of opposing pole (sometimes referred to as a "ground" or "earth"). Current density may be very high at the knife edge, but very low at the grounding electrode. Accordingly, cutting and cauterization only occur at the tip of the instrument with very little or negligible damage to tissues near the other electrode which is spread over a considerably large area.

While monopolar systems are considered safe, the use of these systems includes undesirably passing electrical currents through healthy tissue. As an alternative, bipolar electrical cutting systems are sometimes arranged with both electrodes incorporated in the cutting instrument tip. In this way, electrical current passes from the first electrode, briefly through a small portion of tissue, and thereafter returns at the electrode of opposite pole. The electrical current only interacts with a very small volume of tissue, and specifically with the portion of tissue intended to be manipulated (cut or cauterized). Because of this, bipolar systems are sometimes preferred as more efficient and safe.

Laparoscopic surgical techniques allow for surgical procedures to remove large organs through very small abdominal incisions. In a laparoscopic surgery, small abdominal incisions are made and prepared with special port systems to allow elongate surgical instruments not larger than about 10 mm to about 15 mm in cross-section to be inserted into the abdominal cavity. Video cameras (with lighting), cutting instruments, grabbing tools, among others, are inserted via these abdominal ports and a surgeon manipulates them to operate various organs and tissues. After organs are removed via a laparoscopic surgery, a patient quickly and easily heals as there is considerably less damage to the abdominal wall. Further, operating times are often reduced, thus improving efficiency.

A laparoscopic supracervical hysterectomy can include cutting a uterus away from fallopian tubes, and a blood supply for the uterus. After the uterus is separated from of these and any other connective tissue, the uterine tissue can be severed at a location near the cervix. In common laparoscopic processes, an electrical knife may be used to first resect one side of the uterus, and then the opposite side, to fully sever the circular tissue of the uterus near the cervix. The steps required to manipulate and cut the uterus from separate sides of the organ can be difficult and can require a considerable amount of surgical time.

To improve on positioning a cutting element relative to tissue of a uterus, certain tools have been developed. See for example U.S. Pat. No. 5,078,716 and United States Patent Application 2009/0182324. Among previous tools are instruments that including an open loop wire that can be guided around tissue of a uterus by a specially shaped "introducer." After the "wire" is routed properly, the loop is closed by fastening the wire ends to special hardware provided for such. Application of current causes the uterus to be sectioned in a single plane leaving a preferred cut. The resection step is quick and smooth, but the instrument involves considerable effort to first properly thread the cable around the uterus, and still further to couple the cable ends to the tool sockets in order to realize a closed-loop before application of electrical current.

Other tool alternatives includes a retractable loop that must be placed around the uterus by enlarging the loop and passing the closed loop over the fundus (top) of the uterus. In practice, the need to pass the enlarged closed loop over the fundus of the uterus, and to move the closed loop to isthmus (base) of the uterus, can be challenging.

SUMMARY

Described as follows are surgical cutting instruments and methods, the instruments including a distal end that includes a frame and a cutting element (sometimes referred to herein as a "wire" or "cutting wire"). According to the description, the distal end of the instrument includes a frame that can be extended from and retracted into a lumen of an elongate shaft. When retracted into the lumen, the frame can conform to a relatively straight non-relaxed (retracted) shape that fits within the lumen. In an extended state, the frame adopts a relaxed state that includes a shape suited to support the cutting element and allow the cutting element to be applied to tissue to cut the tissue during a surgical procedure. Preferably, the frame in the extended state supports the cutting element to allow the cutting element to contact tissue and also cauterize tissue, while the frame at least partially surrounds the tissue. The frame can be particularly adapted to support a cutting element so the cutting element can pass through round or lumenal tissue such as an isthmus of a uterus, or another tissue having a closed (e.g., round or circular) circumference; the frame can be shaped in a rounded, e.g., semicircular form and sized to substantially surround the tissue while the cutting element supported at opposite locations of the frame passes through the tissue.

In particular embodiments the cutting element can be moveable relative to the frame in the extended state. Upon extension of the frame, the location of the cutting element relative to the frame can be changed and adjusted. The cutting element can be supported at two separate locations at the distal end of the instrument, and the length of the cutting element between those two locations can be varied and adjusted, as can the tension in the cutting element. In more specific embodiments, the frame can include a channel that extends along a length of the frame and that is adapted to receive the cutting wire.

In one aspect the invention relates to a surgical instrument useful for cutting tissue. The instrument includes: an elongate shaft comprising a lumen extending between an elongate shaft proximal end and an elongate shaft distal end; an inner shaft within the lumen, the inner shaft being capable of longitudinal movement within the lumen; a frame connected to a distal end of the inner shaft, the frame capable of being extended and retracted from the elongate shaft distal end by longitudinal movement of the inner shaft, wherein the frame adopts an extended state when extended from the elongate shaft distal end and a retracted state when refracted into the lumen; a cutting wire comprising a cutting wire distal end connected to the frame at a first location spaced from the inner shaft distal end; and a cutting wire actuator at a proximal end of the instrument that can be manipulated to cause the cutting wire to be selectively moved relative to the frame. The frame in the extended state supports the cutting wire to allow the cutting wire to pass through tissue to cut the tissue, with the cutting wire extending between the first location and a second location on a proximal side of the instrument relative to the first location.

In another aspect the invention relates to a surgical instrument useful for cutting tissue. The instrument includes: an elongate shaft comprising a lumen extending between an elongate shaft proximal end and an elongate shaft distal end; an inner shaft within the lumen, the inner shaft being capable of longitudinal movement within the lumen; a frame connected to a distal end of the inner shaft, the frame capable of being extended and retracted from the elongate shaft distal end by longitudinal movement of the inner shaft, wherein the frame adopts an extended state when extended from the elongate shaft distal end and a retracted state when retracted into the lumen, the frame comprising a channel along a length of the frame; and a cutting wire comprising a cutting wire distal end connected to the frame at a first location spaced from the inner shaft distal end. The cutting wire is capable of being located in the channel.

In another aspect the invention relates to methods of using a surgical instrument as described, for cutting tissue. The method includes: providing a surgical instrument as described herein; with the frame in the retracted state and located in the lumen, passing the surgical instrument through an incision in a patient; extending the frame from the distal end of the elongate lumen such that the frame assumes the extended state; and placing the wire in contact with tissue to cut the tissue. Specific methods can avoid or exclude a step of passing the frame in the extended state and the cutting wire, over a fundus of the uterus to locate the frame on an opposite side of the uterus from the wire.

DETAILED DESCRIPTION

Figure 1A:
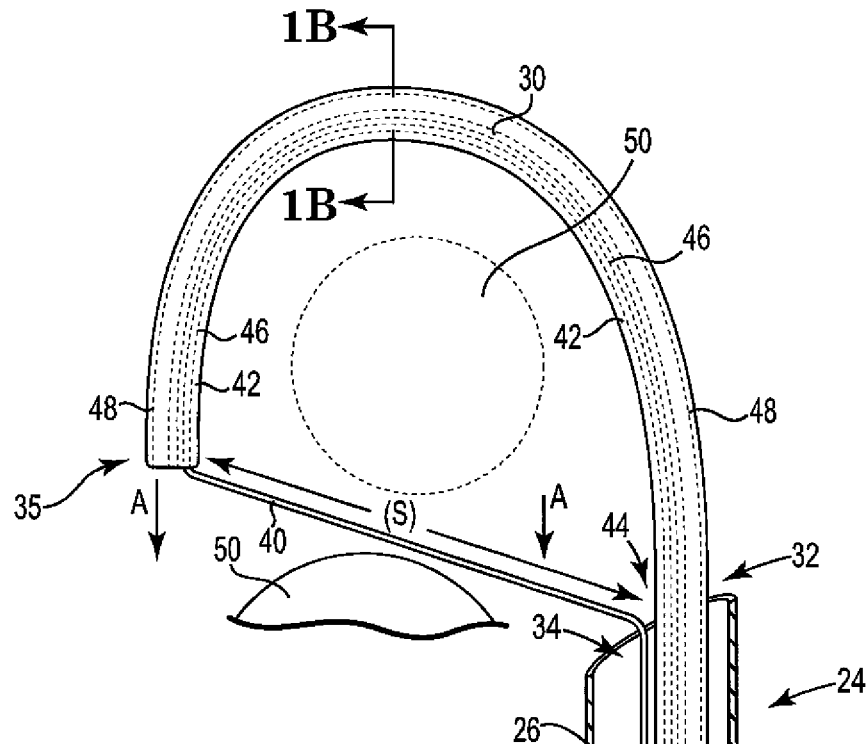
FIG. 1A shows features of a cutting instrument.

The present application relates to a surgical instrument such as a cutting tool having distal end functionality that includes a cutting element (referred to sometimes herein as a "cutting wire" or simply "wire") that may be energized using electricity, ultrasonically, or with heat, etc. The instrument can be useful to cut tissue by applying energy to the cutting wire to improve the ability of the wire to sever tissue. The wire, when energized, can be useful to cut any type of bodily tissue, such as relatively healthy soft tissue, bone or other hard tissue, disease tissue such as cancer or fibroid tissue, or any other similar tissue. The wire may cut the tissue to sever the tissue for removal or repair, and may optionally also cauterize the tissue, particularly if the tissue is vascularized as may be tissue of a uterus, fibroid, polyp, prostate, tonsil, muscle, cancer tissue, connective tissue, fallopian tube, etc. Examples of specific tissue types that may be cut with the described instrument include uterus tissue, prostate tissue, various muscle tissues, tonsils, polyps, other body growths such as fibroids, cancers, and the like.

The instrument can be useful with any surgical technique or method for cutting and optionally cauterizing tissue, many varieties of which are presently known (e.g., a hysterectomy). The instrument can be particularly useful for laparoscopic procedures but may also be useful with non-laparoscopic procedures such as procedures that do not access a patient's internal tissue through a large incision, and therefore do not provide wide access to internal tissue. One example of a non-laparoscopic procedure is a transvaginal procedure.

An exemplary instrument can include a proximal end, a distal end, and a body such as an elongate shaft that extends between the proximal end and the distal end. (As used herein, the term "distal" will generally refer to locations relatively away from a surgeon using the instrument and relatively closer to the patient when the instrument is in use surgically. The term "proximal" will refer to locations relatively closer to the surgeon and relatively farther away from the patient. When referring to a non-linear frame, "distal" means a location relatively farther from the base of the frame and "proximal" means a location closer to the base of the frame.) The distal end of the instrument includes a frame and a cutting wire, both extendible and retractable from an end of the body (e.g., elongate shaft). The proximal end of the instrument can include a handle and actuating mechanisms used to manipulate distal end functionalities such as the wire and the frame. In various contemplated embodiments, the instrument includes an extendable and retractable frame, and a distal end of the cutting wire connects to the frame. Optionally the cutting wire may reside in a channel extending along a length of the frame. Also optionally and preferably the cutting wire is moveable relative to the frame, such as when the frame is in an extended state, by use of a cutting wire actuator at a proximal end of the device.

An instrument can include an elongate shaft that includes a lumen extending between a proximal end of the elongate shaft and a distal end of the elongate shaft. The elongate shaft includes an interior lumen along a length of the shaft, and can be substantially rigid and made of a surgical material such as stainless steel. The exterior and interior diameters of the shaft, and the shaft length, can be suitable for use in a surgical procedure, especially a laparoscopic procedure. For example, an outer diameter of an elongate shaft can be suitable to pass through a standard laparoscopic port placed in a laparoscopic incision, exemplary cross sectional diameters being in a range from about 10 to about 15 millimeters.

Contained within the lumen is an inner shaft that can be moved longitudinally, i.e., distally and proximally, within the lumen. With movement of the inner shaft distally and proximally, a frame connected to a distal end of the inner shaft will be alternately extended and retracted from the lumen, e.g., extending and retracting from an opening at the distal end of the elongate shaft. The inner shaft includes a proximal end and a distal end, with a frame (e.g., a frame base) being connected to the inner shaft distal end. The inner shaft can be any rigid or semi-rigid material (e.g., rigid plastic or metal) capable of connecting to the frame (e.g., the frame base) and being moved distally and proximally to alternately extend and retract the frame relative to the lumen. Contained by or adjacent to the inner shaft or elongate shaft, e.g., along a length of the inner shaft, within the lumen, may optionally be one or more mechanical or electrical connection to a distal end functionality of the instrument, such as a connection to an electrode or cutting wire.

A frame connected to the distal end of the inner shaft is capable of exhibiting an extended state when extended from the elongate shaft distal end. The extended state is sometimes referred to as the "relaxed," "biased," or "natural" state of the frame. The frame is also capable of exhibiting a retracted state when retracted into the lumen. The retracted state may be referred to as a "non-relaxed" state.

The frame can be prepared from one or a combination of materials to produce a frame that is flexible and also resilient, so that the frame in the non-relaxed, retracted state is capable of being deformed from the relaxed state to be contained within the lumen, taking on a shape of the interior of the lumen, e.g., substantially linear or straight. The shape of the frame in the extended state will differ from the shape of the frame in the retracted state. The shape of the extended state will be suitable to support the cutting wire in a manner that allows the wire to be brought into contact with tissue to cut the tissue as described herein.

The frame can be made of any useful material or combination of materials that allows the frame to alternately and reversibly, through multiple cycles, take on the form of the desired extended (relaxed) state, and the desired (un-relaxed) retracted state. Useful materials can be flexible, resilient, and shape-deformable between the retracted state and the extended state. The frame can be formed from one or multiple materials to be biased to adopt the (non-linear, e.g., curved) extended state, with the frame material or materials being sufficiently flexible and resilient to preferably be reversibly and non-permanently deformed upon withdrawal into the lumen to adopt the retracted state. Useful materials include metals and certain plastics that can be formed, molded, heat treated, or thermoformed or thermoset to the extended (relaxed) state, while also being sufficiently strong, flexible, and resilient to be contained in the lumen and also to support a cutting wire in the extended state for cutting tissue. The material, if a plastic, may optionally and desirably be electrically non-conductive or insulating, particularly in embodiments of frames that include a return wire.

Examples of useful polymers are any polymers that are sufficiently stable, resilient, strong, and flexible to function as described. Examples include polyethylene terephthalate (e.g., nylon), polyacrylate, polyolefins, polycarbonate, and similar polymers having mechanical properties including strength, resilience, and flexibility that will make the material useful in a frame as described. In frame embodiments that include an inner metal core surrounded by an insulating material, the insulating material may be any useful insulating material, including any of the polymeric materials mentioned above, and additionally including more flexible and less rigid materials such as insulating silicone rubber, natural and artificial rubbers, polyvinyl chloride, etc.

Examples of metals that can be useful as a frame or as a frame component can include stainless steel or other metals that can be molded, cast, bent, heat-treated, or otherwise formed and treated to make a frame that will exhibit extended and retracted states as described, with useful flexibility, strength, and resiliency. Stainless steel may be used, having a gauge and shape that will provide the desired strength, flexibility, and resiliency in and between the retracted and extended states. Another example of a useful metal is a class of metals known as shape-memory materials, which includes Nitinol. Nitinol is a generic trade name for NiTi alloys that include the materials Nickel (Ni) Titanium (Ti). Advantageously, Nitinol and other shape-memory materials can exhibit fatigue resistance at orders of magnitude higher than other metals or elastic materials. Nitinol alloys can vary in the relative amounts of nickel and titanium, and some useful alloys including nickel and titanium at roughly equal atomic percentages (e.g., 40:60 to 60:40). Nitinol may exhibit both shape memory and superelasticity.

The frame can be functionally flexible and resilient to allow the frame to be repeatedly deformed (e.g., bent, distorted, or the like) and relaxed, by passing reversibly between the extended and the retracted states, while also being sufficiently strong in the extended state to function to support the cutting wire during use for cutting tissue. Optionally, the frame can include an insulating surface, particularly if the frame or cutting wire includes an electrically charged wire. Exemplary frames may include a shape memory (e.g., metal) core surrounded by a polymeric (e.g., plastic) insulating material, and optionally an electrical wire connecting to a cutting wire or other electrode. This type of shape-memory (e.g., metal)-core-plastic-coated-frame exhibits flexibility and resiliency due to the shape-memory core, allowing the frame to be extended and retracted from the distal end of the elongate shaft.

In suitable or preferred embodiments, the frame in the extended state is biased to adopt a shape that supports the wire and allows the wire to be used to cut tissue without undue interference from the frame. That shape of the frame can preferably include a curved, angled, bent, or otherwise non-linear frame portion or frame segment that allows the frame to produce a span between two locations on the distal end of the instrument including at least one location on the frame. When two opposite ends (a distal end and a proximal end) of the cutting wire are associated with (e.g., securely or loosely connected to) the two locations, the cutting wire can extend between the two locations (with the frame in the extended state) without the cutting wire contacting the frame between the ends of the cutting wire.

The first location may be a location on the frame that is distal to the distal end of the inner shaft, and also preferably distal to the frame base, i.e., a location that is distal to the frame base and toward or preferably at or near a distal portion or the distal end of the frame. For example, the first location may be at or near the distal end of the frame or at a distal portion of the frame such as at a distal 10 percent of the length of the frame.

A second location, i.e., a location that contacts or connects to a proximal end of the cutting wire, can be proximal to the first location. Here "proximal" with respect to a location along a length of a curved (extended) frame refers to a location on the frame that is a shorter distance along the curved frame from the frame base (nearer to the frame base) compared to a distance from the frame base to the first location; the second location is located on a proximal side of the first location when the frame is in the retracted state. The second location may be on the frame near the frame base or at the frame base, or may be off of the frame base at the distal end of the inner shaft, or at a distal end of the elongate shaft (e.g., at an opening at the distal end of the elongate shaft).

In certain embodiments, a distal end of the cutting wire connects to the first location, which is at the distal end or the distal portion of the frame, and can preferably be fixed at that location. A proximal end of the cutting wire connects to the second location, and may be either fixed or un-fixed (loose), preferably un-fixed. If un-fixed, the length of the cutting wire between the two locations and between the proximal and distal ends of the cutting wire, or the tension of the cutting wire, may be adjusted by manipulation of a lead connected to the cutting wire and extending to the proximal end of the cutting instrument, e.g., by an actuator at a proximal end of the instrument that connects to the proximal end of the cutting wire. For example, the cutting wire may be adjusted to be approximately taut during cutting to thereby be positioned along a direct line between the first location and the second location; the length of the cutting wire will be about the same as the length of the span between the first location and the second location. See, e.g., FIGS. 1A and 1B. Alternately, the cutting wire need not be taut between the first location and the second location but may be adjusted to be slightly loose during cutting, to contain an amount of slack (see, e.g., FIG. 3E), in which instance the length of the cutting wire will be greater than the distance of the span between the first location and the second location.

According to preferred embodiments of the described instruments, the distal end of the cutting wire can be fixedly attached to the first location, at a distal end of the frame, and the proximal end of the cutting wire can be loosely associated with or connected to the second location, which is at or near the base of the frame or the distal end of the elongate shaft. In these embodiments, the length of the cutting wire extending between the first location and the second location can be adjusted, i.e., increased (lengthened) or decreased (shortened) as desired by a surgeon or other user of the instrument, preferably by manipulating an actuating mechanism at the proximal end of the instrument.

According to certain more particular embodiments, a frame can adopt an extended state that includes a shape suited to support the cutting wire and at the same time allow the cutting wire to contact and pass through tissue to be cut during a surgical procedure, preferably while the frame does not contact the tissue that is being cut in an interfering manner. The frame may contact tissue that is adjacent to the tissue being cut, and may even contact tissue that has been cut (already severed) after the cutting wire has passed through that tissue, but is shaped to surround and to not contact the tissue of the specific tissue mass or organ (e.g., uterine isthmus) as that tissue is being cut. The frame may generally be shaped to support the cutting wire during a cutting step while not interfering with movement of the wire through the tissue that is being cut.

Certain exemplary frame structures can be particularly adapted to support the cutting wire so the cutting wire can be passed through specific tissue masses (e.g., a fibroid) or organs (e.g., a uterus) by movement of the frame in a direction to cause the wire to pass into and through the tissue mass or organ in a direction that results in the frame trailing behind the cutting wire; the cutting wire and frame can be moved together in one direction toward tissue to cause the cutting wire to pass through the tissue while the frame moves toward the tissue but does not contact the tissue but instead surrounds the tissue. (See FIGS. 1A, 2A, 3D, and 3E, showing arrows "A" to indicate a direction of movement of the frame and wire during cutting.) In frame structures designed to cut a round or circular tissue mass or a lumenal organ, such as an isthmus of a uterus or another tissue having a closed (e.g., round or circular) circumference, the frame can be shaped in a rounded, e.g., semicircular or approximately semicircular form and sized to substantially surround the rounded tissue mass or lumenal organ while the cutting wire is supported at opposite locations of the frame and passes through the tissue mass or organ. The wire (optionally taut or with slack) extends the distance of a span between a distal end or distal portion of the frame, and a base of the frame or nearby location (e.g., at the elongate shaft distal end or inner shaft distal end). The distance or length of the span (measured directly from the first location to the second location) can be at least as large as a dimension (e.g., diameter) of the rounded tissue or lumenal organ that will be severed by the cutting wire. In a healthy human female, a diameter of an isthmus of a uterus may be in a range from about 2 to about 4 centimeters. The dimension may be larger if a fibroid is present. For use in cutting an isthmus of uterus, a frame can have a span between the first location and the second location (e.g., an end of the frame and a base of the frame) in a range from 1 centimeter to 6 centimeters, e.g., from 1.5 to 4.5 centimeters.

The cutting element (referred to generally as a "cutting wire" or "wire") can be any cutting element useful to cut living tissue (e.g., soft tissue, muscle, bone, etc., of a human or animal). The wire may be sharpened or unsharpened and may be energized by electricity, heat, ultrasound, etc., as is typical of surgical cutting tools. To cut and also cauterize tissue, a cutting element may be energized by high frequency electrical current, and may be of a monopolar or a bipolar type, e.g., containing a single electrode or two electrodes. Desirably, the wire can be capable of cutting hard or soft tissue without placing too great of a load on the wire; the load may be sufficiently low to avoid substantial deformation of the wire and the frame during cutting; the energy in the wire is effective to allow the wire to easily cut and pass through tissue with little load being placed on the wire.

The cutting wire attaches at two locations at the distal end of the surgical instrument. Preferably, a distal end of the cutting wire can attach to the frame at a first (distal) location and a proximal end of the wire attaches at a second more proximal location at the distal end of the instrument. When the inner shaft is extended, the wire can be extended between the two locations to form an extended wire that can be contacted with tissue for cutting. The cutting wire may be taut or loose (containing some slack) and the tautness, looseness, tension, and length of the cutting wire between the first location and the second location may be controlled by an actuating mechanism at a proximal end of the device.

The wire may be energized by heat, electricity, ultrasonic energy, or any other form of energy to improve the ability of the cutting wire to pass through and cut tissue, optionally to also cauterize the tissue. According to known and preferred methods and cutting tools, the wire can be electrically conductive and electrically charged either in a monopolar manner or a bi-polar manner, i.e., at one or two electrodes. In monopolar embodiments, the wire can contain a single pole or electrode. Electricity will flow from the wire to tissue (at a different voltage), causing the tissue to be cut and preferably to be cauterized. The electrical current passing from the cutting wire will pass into the tissue being cut, and will then disperse and flow through the patient's tissue to a ground connection.

In a bipolar embodiment, the distal end of the cutting instrument will have two poles, i.e., two electrodes. Electricity can flow between the electrodes, through tissue adjacent to or between the two electrodes, to cut and preferably cauterize the tissue.

As an example, one electrode can be a cutting wire and a second electrode may be at a separate location of the distal end of the cutting instrument. Alternately, two electrodes can be located on a single cutting wire extending across the span of the frame. Electricity will flow from the first electrode to the second electrode to pass through desired tissue to be cut, cutting and preferably cauterizing the tissue.

The design of the present frame and cutting wire can allow for improved and in cases advantageous surgical cutting methods, especially of rounded or lumenal tissue (e.g., lumenal organs such as a uterine isthmus), preferably in laparoscopic surgical procedures. For cutting a uterus, for example, past electrical cutting and cauterizing instruments have required that a cutting wire be placed around a base of a uterus and tightened around the base. One manner of placing the wire around the base of the uterus was to pass a loose end of the wire around the base of the uterus, then grasp the loose end with a tool to form a closed loop that can be tightened about the uterus at tissue of a uterine isthmus. An alternate manner is to produce a large closed loop of a wire that is capable being extended from a distal end of a surgical tool, passed during a surgical procedure all the way over the top of the uterus (over and around the fundus) as a closed loop, and then moved in an inferior and posterior direction to the base of the uterus (see United States Patent application 2009/0182324). The step of passing an expanded, closed loop over the fundus of a uterus during a surgical procedure can prove difficult.

In contrast to these and other previous devices and methods, the described devices and methods include a surgical instrument that has a frame and cutting wire at a distal end of a cutting instrument, with the cutting wire supported by the frame in a manner that allows the cutting wire to contact and preferably cauterize round or lumenal tissue without having to pass a loose end of the cutting wire about the tissue, or to pass a closed cutting wire loop over the tissue (e.g., fundus of a uterus). According to described devices, a cutting wire supported by a frame as described can be brought to contact tissue of a uterine isthmus (or other round or lumenal tissue) without requiring a closed loop defined by the frame and the cutting wire to be passed over the fundus of the uterus and then brought down to the isthmus of the uterus. Instead, the frame can be used to advance the cutting wire in a direction to contact tissue (e.g., of the uterine isthmus) by positioning the cutting wire and frame adjacent to the tissue (e.g., isthmus), with the cutting wire positioned between the tissue and the frame. The frame can then be used to advance the wire toward, into contact with, and through the tissue (e.g., isthmus). The frame can support the cutting wire and pass the cutting wire through the lumenal tissue or organ, while the frame does not contact the lumenal tissue or organ, such as by surrounding the lumenal tissue or organ.

Non-limiting examples of instruments and method of the present description include the following. FIG. 1A shows surgical instrument 10, which comprises elongate shaft 20 that includes elongate shaft proximal end 22, elongate shaft distal end 24, and lumen 26 extending therebetween. Inner shaft 41 extends within lumen 26. Inner shaft distal end 44 of inner shaft 41 connects to and supports frame 30 at base 32 such that inner shaft 41 and can be moved longitudinally (proximally and distally) within lumen 26 to cause frame 30 to be extended from and retracted back into lumen 26 at opening 34 of elongate shaft distal end 24.

Also contained within lumen 26 is wire lead 33, which connects cutting wire 40 to a proximal end of instrument 10 (e.g., to an actuating mechanism (not shown) for controlling the length of or tension applied to cutting wire 40, and allowing for a user to control energy applied to cutting wire 40). As illustrated wire lead 33 is located in lumen 26 and extends along the length of lumen 26 between a distal end 24 of elongate shaft 20, and proximal end 22 of elongate shaft 20. Alternately, wire lead 33 could be located elsewhere, such as (moveably located) within a separate lumen extending along a length of elongate shaft 20, embedded (moveably) within a wall of elongate shaft 20, embedded (moveably) in inner shaft 41, exterior to elongate shaft 20, or at any other position that allows wire lead 33 to connect to a proximal end of connecting wire 40, and thereby connect connecting wire 40 to a proximal end of instrument 10, e.g., at an actuating mechanism (not shown) for controlling wire 40.

Figure 1B:
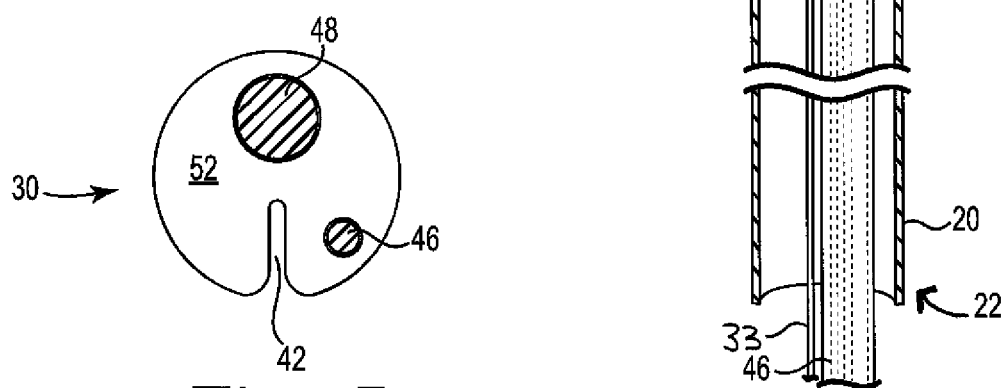
FIG. 1B shows a cross section of a frame of a cutting instrument.
Figure 1C:
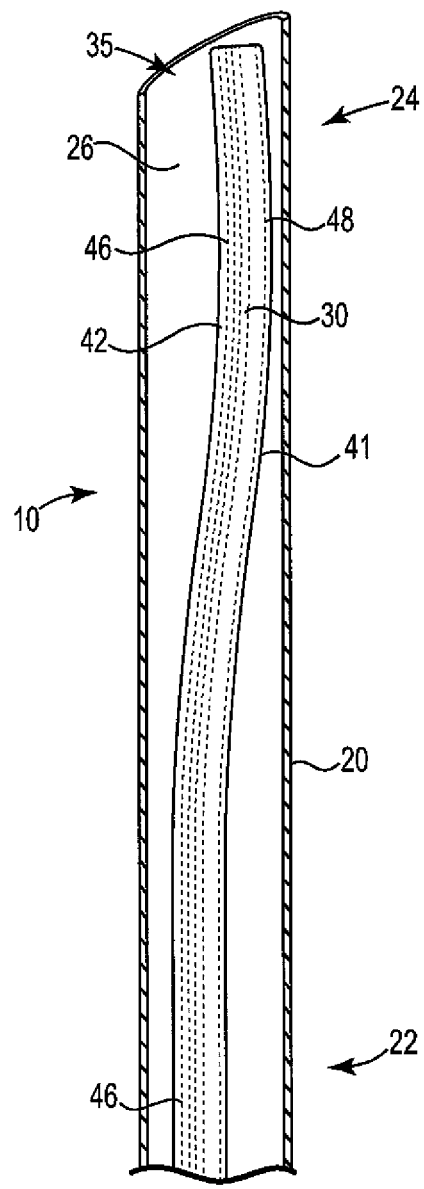
FIG. 1C shows a distal portion of a cutting instrument.

Referring to FIGS. 1A and 1C, frame 30 when retracted resides within lumen 26. Frame 30 within lumen 26 is deformed to the retracted state, which is substantially straightened and linear to approximate the interior space within lumen 26. When extended, frame 30 takes on the extended form and supports cutting wire 40 for use in cutting and optionally cauterizing tissue. Frame 30 in the extended form can take on a non-linear (e.g., curved, such as semi-circular) form that attaches at frame base 32 to distal end 44 of inner shaft 41 and then extends away from distal end 24 of elongate shaft 20 along a path that includes a curve or other non-linear form. The non-linear form can be curved, angled, or otherwise non-linear, terminating at frame distal end 35 in a manner that creates a space or opening between frame 30 and cutting wire 40, including a span (S) between frame distal end 35 and frame base 32 and adjacent structures including opening 34. Frame 30 and cutting wire 40 create a closed non-circular loop that can be extended from distal end 24 of elongate shaft 20, then retracted back into elongate shaft 20. Cutting wire 40 extends from a location at or near distal end 24 of elongate shaft 20 (a second location), to a more distal location on frame 30 (a first location) such as at or near frame distal end 35. A distal end of cutting wire 40 may fixedly attach to frame distal end 35, extend across span (S) defined by extended frame 30, with a proximal end of cutting wire 40 attaching (e.g., loosely) at or near base 32 of frame 30 or distal aperture 34 of elongate shaft 20. Because the proximal end of cutting wire 40 is (preferably) loosely connected to the second (proximal) location, the length of cutting wire 40 between the first location and the second location can be varied and adjusted. If cutting wire 40 is monopolar, (e.g., a single electrode in a monopolar electrode embodiment), only a single wire lead 33 connects to one side (e.g., a proximal end) of cutting wire 40 (see FIG. 2A and 2B). Alternately, if cutting wire 40 is bipolar (e.g., contains more two opposed electrodes), wire lead 33 can connect to one side (e.g., a proximal end) of cutting wire 40 while a second wire lead (e.g., return wire 46), carrying a different polarity or voltage, can connect to the second side (e.g., distal end) of cutting wire 40. See FIG. 1A.

Still referring to FIG. 1A, extending from elongate shaft distal end 24, through aperture 34, is frame 30, which connects at frame base 32 to inner shaft distal end 44. Cutting wire 40 is supported at a distal cutting wire end at frame distal end 35, and is supported at a proximal cutting wire end at aperture 34. Features of this illustrated embodiment of frame 30, not all of which are required, include optional channel 42, optional return wire 46 and optional shape memory core 48. Channel 42 is an optional feature extending along a length of frame 30 on the inner side of the curved frame structure when extended. Channel 42 is adapted to receive and contain cutting wire 40 when frame 30 is in a retracted (at least substantially straightened) state, within lumen 26. Placing cutting wire 40 within channel 42 can assist, for example, in allowing frame 30 to fit within lumen 26 when retracted.

Optional return wire 46 is an electrically conductive wire or lead that connects to a distal end of cutting wire 40 (and connects at an opposite end to a proximal end of the instrument). Return wire 45 is included in an instrument that includes an electrically-charged bipolar cutting element such as embodiments of cutting wire 40 that include two electrodes. Return wire 46 is a component of a bipolar set of two opposing electrodes (of cutting wire 40), with other components including wire lead 33 and electrodes (not specifically shown) of cutting wire 40, wherein cutting wire 40 is a bipolar electrical cutting or wire.

Optional shape memory core 48 can be a shape memory material such as Nitinol, a rigid and flexible and resilient plastic material, or a metal, any one of which can be molded, heat-formed, heat-treated, or otherwise formed or processed to be biased to adapt to the extended state when relaxed.

In the illustration at FIG. 1A, frame 30 is shown in an extended (natural or relaxed) state, which is the curved shape to which frame 30 is biased. In this extended state frame 30 extends from opening 34 of distal end 24 and adopts the illustrated curved, semi-circular extended state wherein cutting wire 40 extends across span (S); a distal end of cutting wire 40 is located at frame distal end 35 and a proximal end of cutting wire 40 is located near frame base 32, passing through opening 34. Cutting wire 40, between its proximal and distal ends and extending across span (S), can be loose, taut, or semi-taut, as desired. Optionally and preferably, the length of cutting wire 40 between the cutting wire distal end and the cutting wire proximal end, alternately the amount of tension in cutting wire 40, can be controlled by manipulating an actuator at a proximal end of the instrument. Functionally, the length and tension of cutting wire 40 with frame 30 in the extended state can be sufficient to allow cutting wire 40 to cut and optionally cauterize tissue (50) when cutting wire 40 is contacted with and passed through tissue.

FIG. 1B is a cross section of frame 30. As illustrated, frame 30 includes shape memory (e.g., a useful metal) core 48, return wire 46, and insulator 52 surrounding both of those. Return wire 46 is optional and need not be present in a device wherein cutting wire 40 is a monopolar electrical cutting or wire. Core 48 is also optional, as insulator 52 can alternately function as a shape memory material. For example, insulator 52 functions to embed and insulate electrical return wire 46 from tissue during use, and, therefore can be an electrically insulating material such as a polymeric material. Insulator 52 can also function as a shape memory material if insulator 52 is a polymeric material such as a molded, thermoset, thermoformed, or heat-formed polymer that can be biased to adopt to the extended state when allowed to relax, and is sufficiently resilient, flexible, rigid, and strong, to be cycled repeatedly between the extended state and the retracted state.

FIG. 1A shows frame 30 in an extended state in which frame 30 is capable of supporting cutting wire 30 for cutting tissue. In this extended form frame 30 is relaxed to adopt to its biased, relaxed, extended state. In contrast, FIG. 1C shows frame 30 in a retracted state, in which frame 30 is retracted into lumen 26 and is in a non-relaxed, stressed state that causes frame 30 to be straightened or substantially straightened. Optionally and preferably, when retracted, cutting wire 40 can be located in channel 42 to allow retracted frame 30 to fit within lumen 26.

Figure 2A:
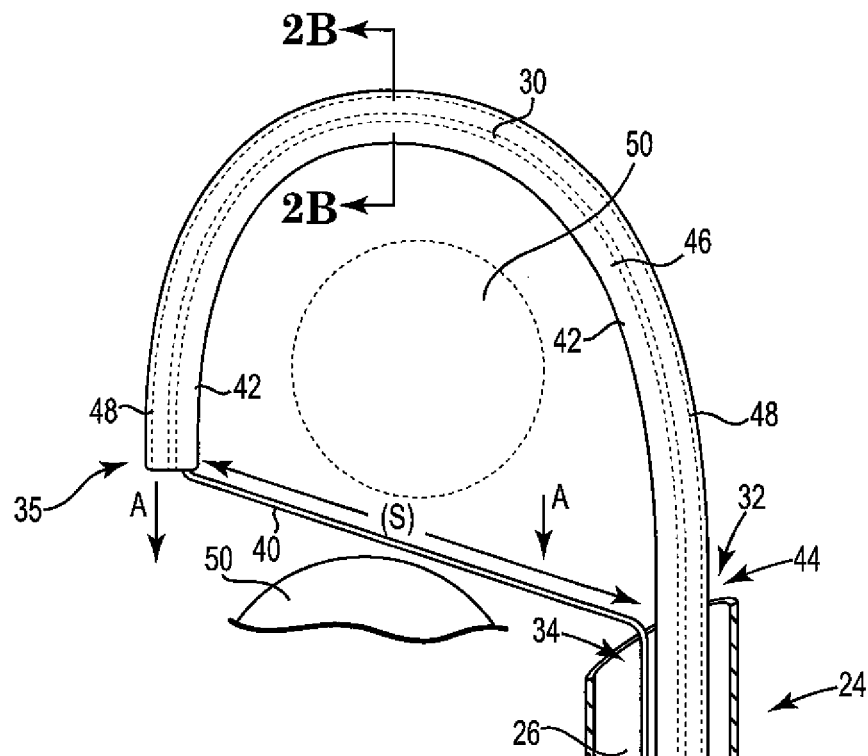
FIG. 2A shows features of a cutting instrument.
Figure 2B:
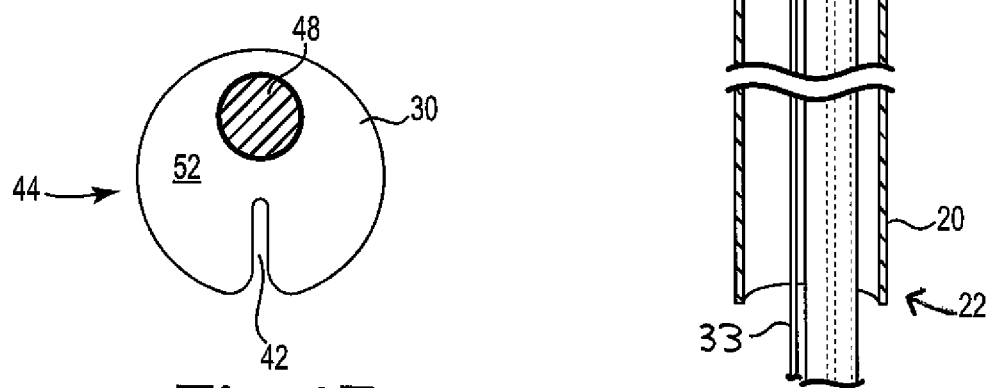
FIG. 2B shows a cross section of a frame of a cutting instrument.

FIGS. 2A and 2B show another embodiment of instrument 10, similar to instrument 10 of FIGS. 1A, 1B, and 1C, and modified to include monopolar cutting wire 40 that extends to and terminates at frame distal end 35; frame 30 of instrument 10 at FIGS. 2A and 2B does not include return wire 46. As such, cutting wire 40 of FIGS. 2A and 2B can be a monopolar electrical cutting and cauterizing wire as opposed to a bipolar electrical cutting and cauterizing wire shown at FIGS. 1A, 13, and 1C. Other features of instrument 10 of FIGS. 2A and 2B can be the same as in instrument 10 of FIGS. 2A, 2B, and 2C.

Referring to FIGS. 3A through 3E, illustrated are exemplary steps of an embodiment of a method of cutting and removing tissue by use of a cutting instrument (e.g., 10) as described herein. At FIG. 3A, surgical cutting instrument 10 is passed through tissue 60, e.g., abdominal tissue, at an incision at which laparoscopic port 62 is placed. As shown, instrument 10 is inserted through port 62 while frame 30 is in a retracted state, retracted within lumen 26 of elongate shaft 20. Distal end 24 is advanced within the patient toward tissue to be cut, which as illustrated is tissue of uterus 50, preferably supracervical tissue of the uterus, which is adjacent to cervix 51 and on an opposite side of cervix 51 relative to vaginal tissue 52, i.e., at a "base" or "neck" of uterus 50 (also referred to as tissue of the uterine isthmus). Desirably, a surgeon will also prepare uterus 52 for removal, such as by disconnecting any connective tissue or fascia that supports the uterus relative to adjacent tissue. Fallopian tubes (not shown) may either be severed to allow ovaries to be left in the patient, or may be intact and disconnected from connective tissue and fascia that hold the fallopian tubes and uterus in place.

Figure 3A:
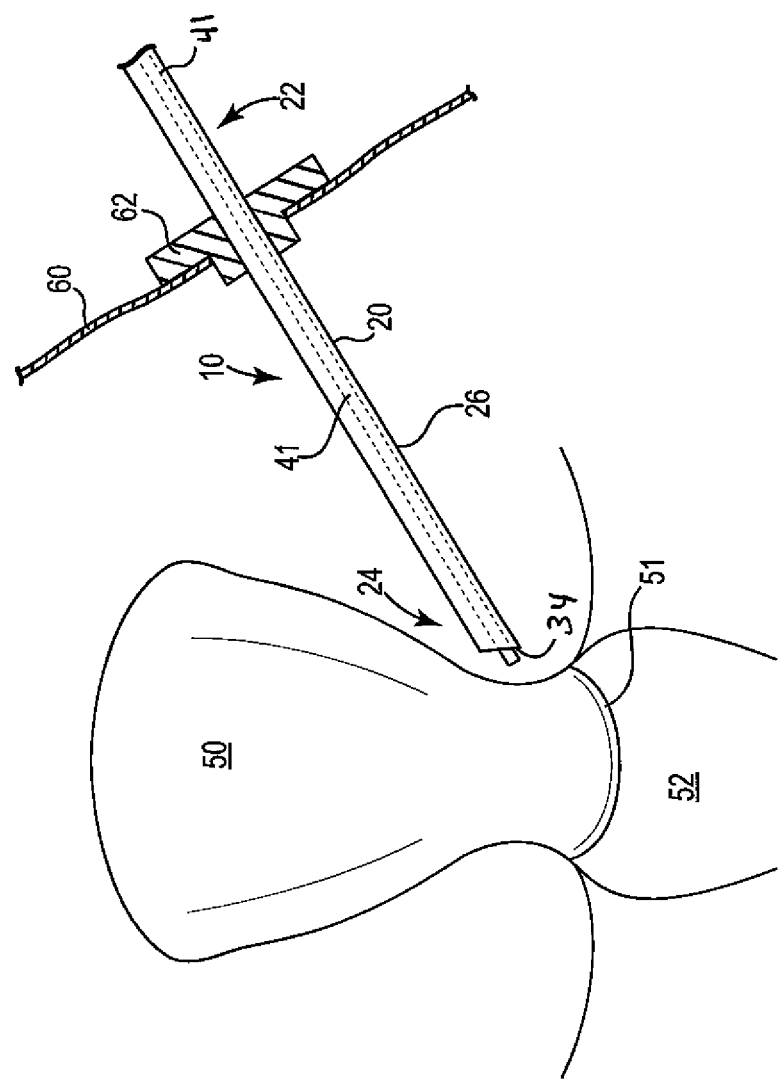
FIGS. 3A through 3E illustrate features of a cutting procedure.
All figures are not to scale.
Figure 3B:
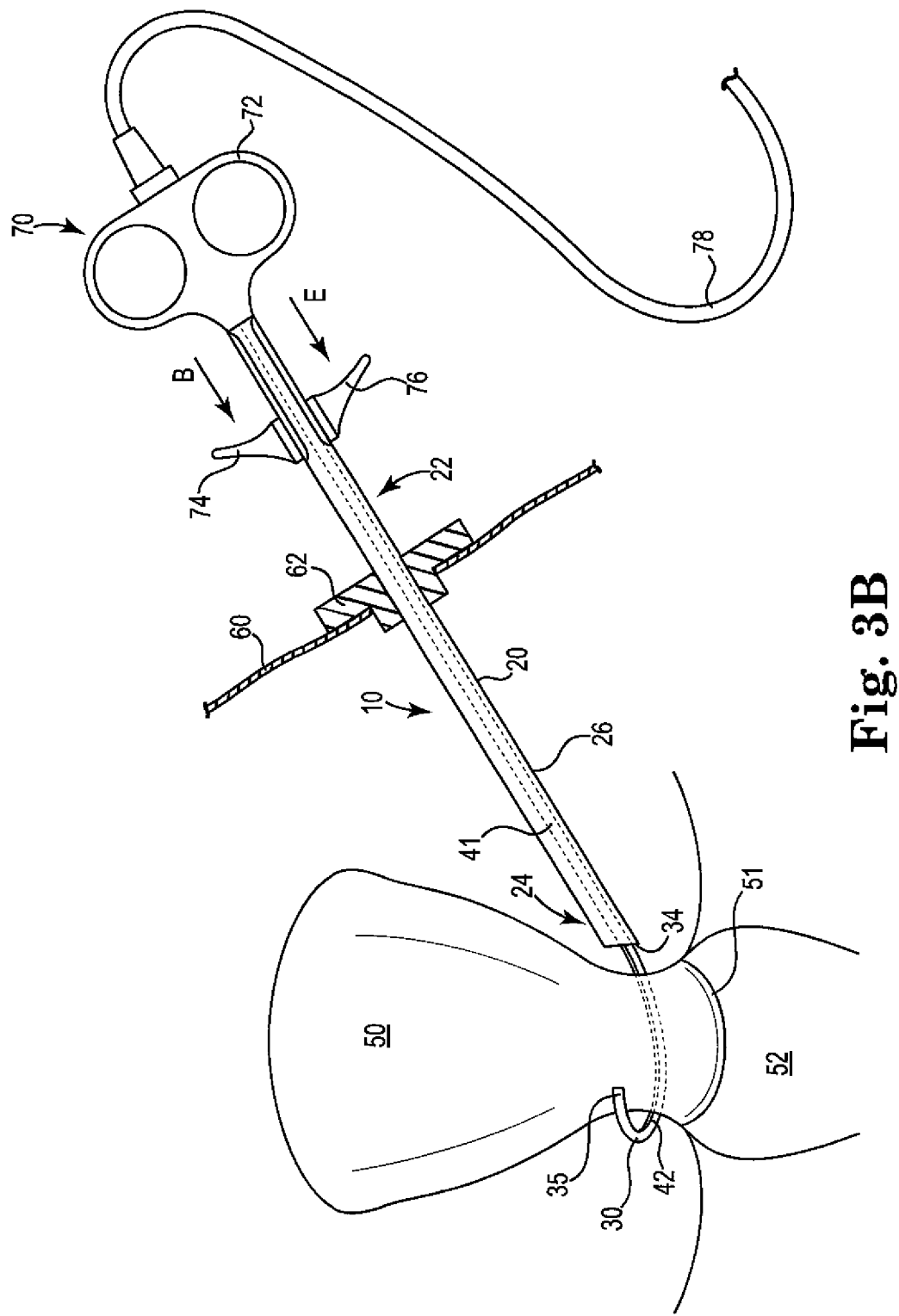

Referring to FIG. 3B, illustrated is proximal end 70 of instrument 10, which includes handle (e.g., finger loops) 72, frame actuator 74, cutting wire actuator 76, and electrical lead or leads (as illustrated, two leads) 78. Electrical leads 78 can (as illustrated) include one lead that extends to a first pole of cutting wire 40 (this first lead may be wire lead 33); a second lead is optional and can extend to and connect to a second pole of cutting wire 40, such as through return wire 46.

Still referring to FIG. 3B, after or upon desired placement of distal end 24 adjacent to the base (isthmus) of uterus 50, frame actuator 74 and cutting wire actuator 76 can be manipulated (e.g., moved distally, see arrow B and arrow E) to cause frame 30 and cutting wire 40 to extend from opening 34 of elongate shaft 20. According to the illustrated embodiment, cutting wire 40 remains positioned within channel 42 of frame 30 as cutting wire 40 and frame 30 extend to the extended state. In the extended state, frame 30 adapts a curved shape that extends in a semi-circular or otherwise curved shape around lumenal tissue (tissue of the uterine isthmus, as illustrated) without requiring contact between frame 30 and the tissue. See FIG. 3E.

Figure 3C:
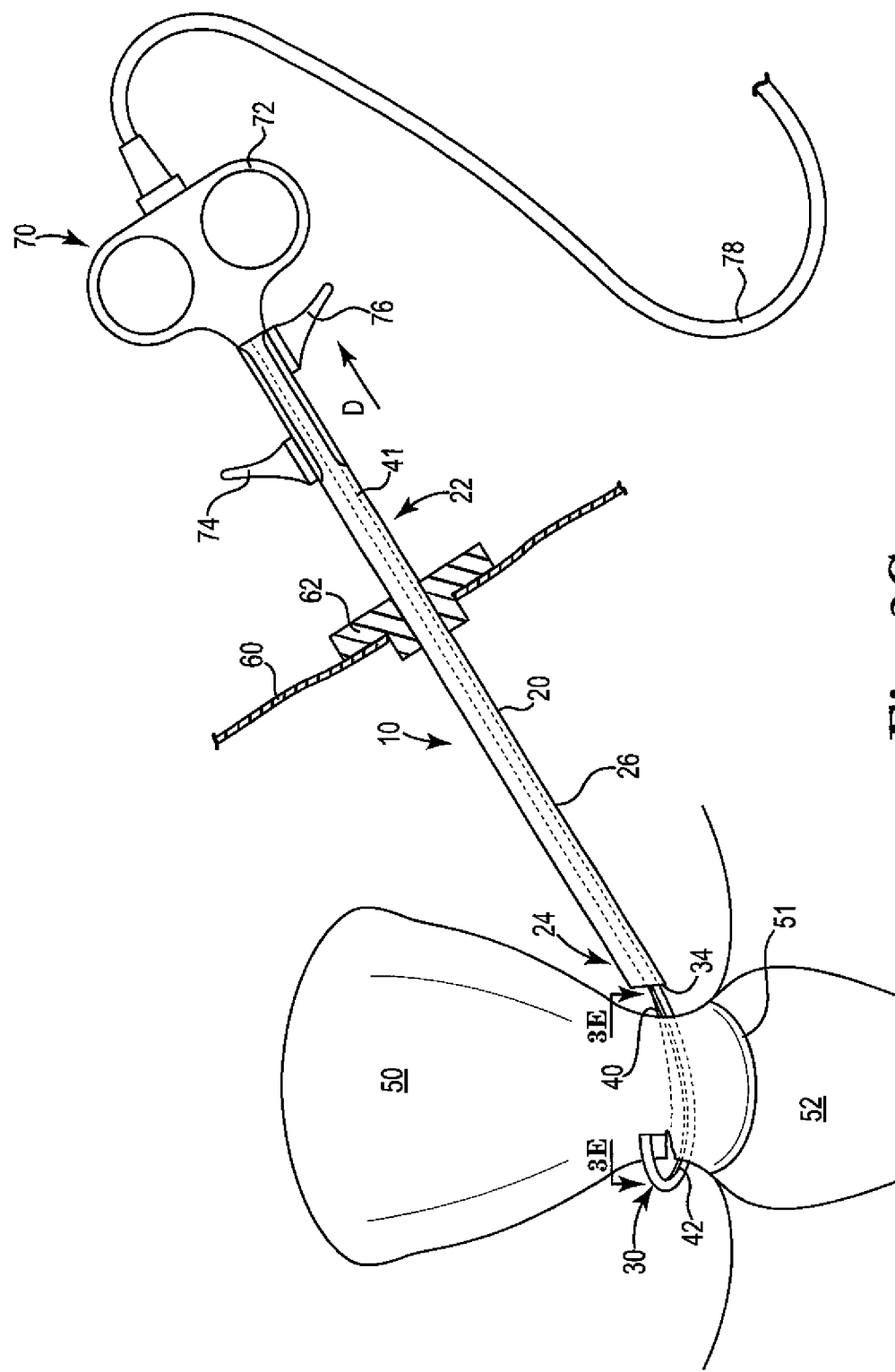
Figure 3D:
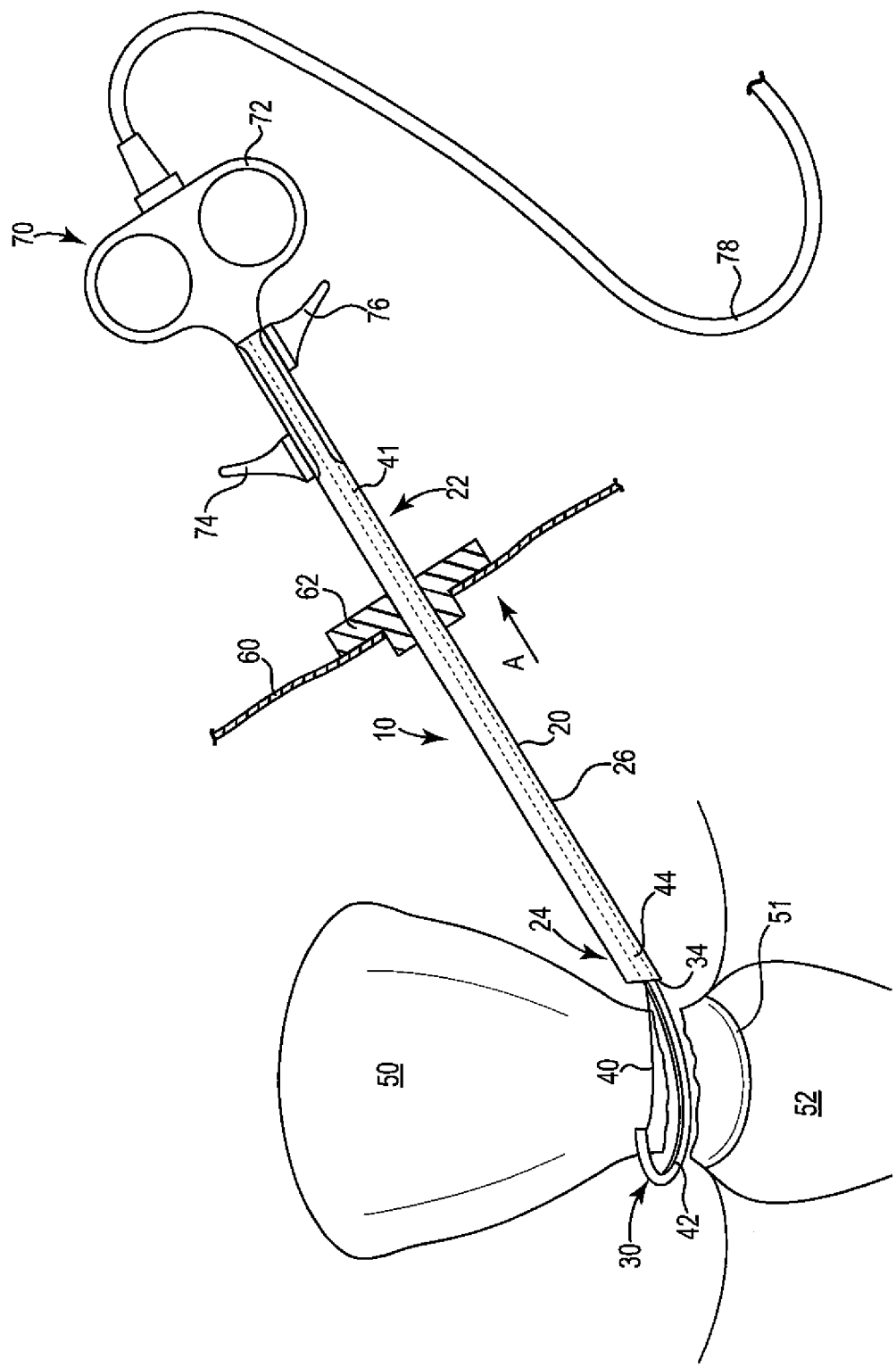
Figure 3E:
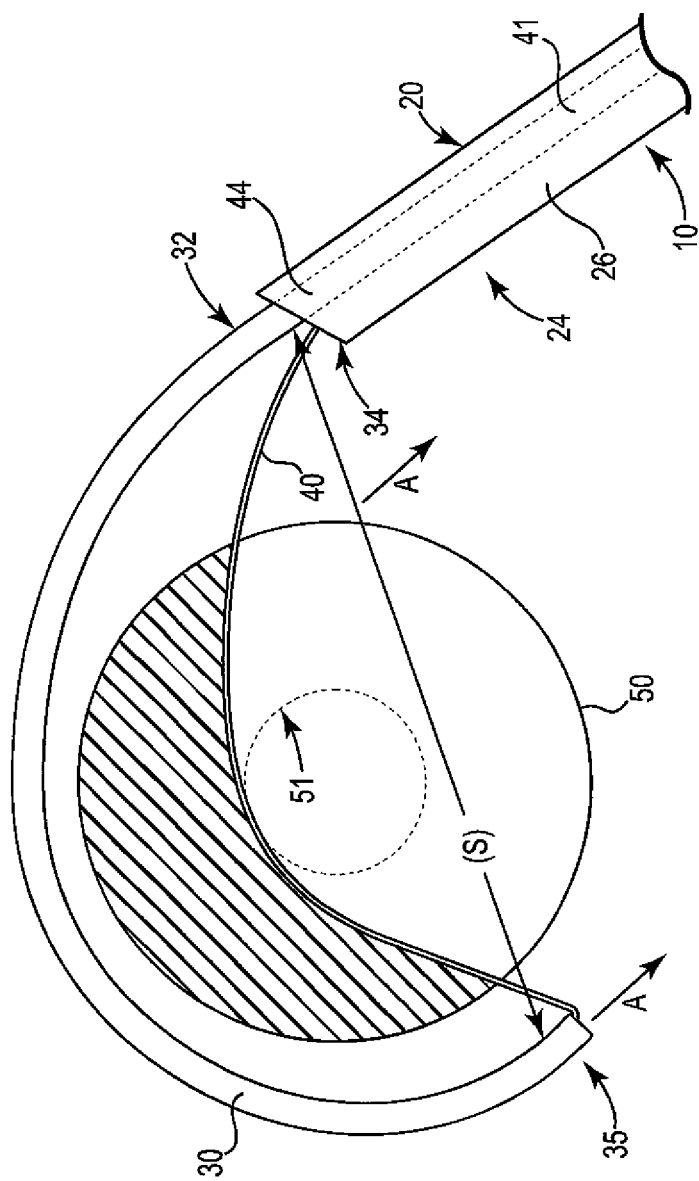

With frame 30 in a desired extended state, a surgeon may extend wire 40 from channel 42 of frame 30, e.g., by use of cutting wire actuator 76, specifically (as illustrated), by pulling cutting wire actuator 76 in a proximal direction (see arrow D at FIG. 3C). FIG. 3C shows instrument 10 with frame 30 in an extended state, and wire 40 being moved out of channel 42, supported across a span (S) of frame 30, adjusted to a desired length, and optionally tensioned, by manipulation of cutting wire actuator 76. The length or amount of tension placed on cutting wire 40 can be as desired and as necessary to allow cutting wire 40 to cut and optionally cauterize tissue of uterus 50. At FIG. 3D, instrument 10 is advanced proximally, in a direction of arrows A to cause cutting wire 40 to pass through and optionally and preferably cauterize tissue of uterus 50, severing uterus 50 at a supracervical location (e.g., at the uterine isthmus) relative to cervix 51 and vagina 52. After uterus 50 is severed at the desired location, e.g., isthmus, frame 30 and cutting wire 40 can be retracted back into channel 26 of elongate shaft 20 and elongate shaft 20 can be withdrawn from the patient, back through laparoscopic port 62.

While the present description emphasizes a method of cutting tissue of a uterine isthmus in a hysterectomy, the described instruments and methods can be of use for cutting any hard or soft tissue at any bodily location. The methods can be particularly useful in laparoscopic procedures by which a large organ or tissue mass may be removed by use of one or a couple (two or three) very small abdominal incisions. In an exemplary laparoscopic surgery, two or three small abdominal incisions are made and prepared with special port systems to allow elongated surgical instruments, including a cutting instrument as described, to be inserted into the abdominal cavity. Other instruments that may be useful include a video camera, lighting tool, grabbing tool, retractors, a tissue removal tool (e.g. "morcellating" tool), among others, inserted via these abdominal ports for use by a surgeon to operate on various organs and tissues.

According to certain specific steps, a laparoscopic supracervical hysterectomy that involves the present surgical cutting tool can include steps of laparoscopically cutting a uterus away from supportive tissue (e.g., muscle, fascia), optionally cutting fallopian tubes (if ovaries are desirably left in the patient), and cutting off a blood supply for the uterus. After the uterus is separated from these and any other connective tissue, the uterine tissue can be severed at a location near the cervix, preferably at supracervical location such as a uterine isthmus, using a surgical cutting tool as described herein.

In the cutting step, the described instrument can be passed through a laparoscopic port with the frame in the retracted state within the lumen of the elongate shaft. Once the distal end of the elongate shaft is located as desired, the frame can be extended, preferably with the cutting wire remaining in a channel of the frame. The frame can be passed behind tissue of the urinary isthmus and advanced to partially surround that tissue. With the cutting wire removed from the channel of the frame, the frame and cutting wire can be advanced in a direction that moves the frame and the cutting wire together at once toward the tissue of the urinary isthmus, to cause the cutting wire to pass through the tissue while the frame moves toward the tissue and surrounds the tissue.

Advantageously, the method can be performed without a step of passing the distal end of the frame and cutting wire in the extended state, over the fundus of the uterus to locate the frame on an opposite side of the uterus from the wire.

The invention claimed is:

1. A surgical instrument useful for cutting tissue, the instrument comprising:
    an elongate shaft comprising a lumen extending between an elongate shaft proximal end and an elongate shaft distal end,
    an inner shaft within the lumen, the inner shaft being capable of longitudinal movement within the lumen, the inner shaft having a proximal end and a distal end,
    a frame having a proximal end and a distal end, the frame comprising a frame base at the proximal end of the frame, the frame base connected to the distal end of the inner shaft, the frame including a channel, the frame capable of being extended and retracted from the elongate shaft distal end by longitudinal movement of the inner shaft, wherein, when the frame is in a retracted state, the frame is disposed within the lumen of the elongate shaft, wherein, when the frame is in an extended state, the frame is disposed out of the lumen of the elongate shaft, the frame having a curved portion when the frame is in the extended state,
    a cutting wire having a distal end and a proximal end, the distal end of the cutting wire being coupled to the distal end of the frame, wherein, when the frame is in the retracted state, a portion of the cutting wire is located within the channel, wherein, when the frame is in the extended state, the cutting wire is configured to extend from a first location at the distal end of the frame to a second location proximate to the elongate shaft distal end,
    a cutting wire actuator operatively coupled to the proximal end of the cutting wire, the cutting wire actuator configured to move the cutting wire relative to the frame, wherein, when the frame is in the extended state, the cutting wire actuator is configured to move the portion of the cutting wire to a location outside of the channel.

2. The instrument of claim 1 wherein, in response to the frame being moved to the extended state, the cutting wire actuator is configured to decrease a length of the cutting wire between the first location and the second location.

3. The instrument of claim 1 wherein a length of the cutting wire between the first location and the second location defines a span such that the wire extending across the span is capable of cutting through tissue of a uterine isthmus while the curved portion of the frame at least partially surrounds the tissue.

4. The instrument of claim 3 wherein the span has a length in a range from 1 centimeter to 6 centimeters.

5. The instrument of claim 1 wherein, in response to the frame being moved to the extended state to at least partially surround tissue of a uterine isthmus, the cutting wire actuator is configured to advance the cutting wire toward the tissue of a uterine isthmus by decreasing a length of the cutting wire between the first location and the second location.

6. The instrument of claim 1 wherein the frame is biased to the curved portion.

7. The instrument of claim 1 wherein the frame in the extended state is configured to allow the cutting wire to be brought into contact with tissue of a uterine isthmus without requiring the frame and the cutting wire to be located on opposite sides of the tissue.

8. The instrument of claim 7 wherein the curved portion of the frame is configured to partially surround the tissue as the cutting wire cuts the tissue.

9. The instrument of claim 1, wherein, when the frame is in the extended state, the cutting wire actuator is configured to move the cutting wire to a location outside of the channel by decreasing a length of the cutting wire between the first location and the second location.

10. A surgical instrument useful for cutting tissue, the instrument comprising
an elongate shaft comprising a lumen extending between an elongate shaft proximal end and an elongate shaft distal end,
an inner shaft within the lumen, the inner shaft being capable of longitudinal movement within the lumen, the inner shaft having a proximal end and a distal end,
a frame having a proximal end and a distal end, the frame comprising a frame base at the proximal end of the frame, the frame base connected to the distal end of the inner shaft, the frame capable of being extended and retracted from the elongate shaft distal end by longitudinal movement of the inner shaft, wherein, when the frame is in a retracted state, the frame is disposed within the lumen of the elongate shaft, wherein, when the frame is in an extended state, the frame is disposed out of the lumen of the elongate shaft, the frame having a curved portion when the frame is in the extended state, the frame comprising a channel located on an outer surface of and along a length of the frame,
a cutting wire having a distal end and a proximal end, the distal end of the cutting wire being coupled to the distal end of the frame, wherein, when the frame is in the extended state, the cutting wire is configured to extend from a first location at the distal end of the frame to a second location proximate to the elongate shaft distal end, and
a cutting wire actuator operatively coupled to the proximal end of the cutting wire, the cutting wire actuator configured to move the cutting wire relative to the frame,
wherein, when the frame is in the retracted state, a portion of the cutting wire is disposed within the channel with the frame in the retracted state,
wherein, when the frame is in the extended state, the cutting wire actuator is configured to decrease a length of the cutting wire between the first location and the second location causing the portion of the cutting wire to be disposed outside of the channel.

11. The instrument of claim 10 wherein the channel has a depth extending from an inner surface of the frame in a direction toward a center of the frame, when viewed in cross section.

12. The instrument of claim 10 further comprising a frame actuator, separate from the cutting wire actuator, the frame actuator configured to move the frame between the retracted state and the extended state.

13. The instrument of claim 10 wherein the frame comprises an insulating polymeric material and the channel is formed in the insulating polymeric material.

14. The instrument of claim, 10 wherein the frame includes a return wire.

15. A method of cutting tissue, the method comprising
providing the surgical instrument as recited at claim 1,
with the frame in the retracted state and located in the lumen, passing the surgical instrument through an incision in a patient,
extending the frame from the elongate shaft distal end to place the frame in the extended state,
placing the cutting wire in contact with tissue to cut the tissue by moving the cutting wire actuator in a proximal direction, wherein, in response to moving the cutting wire actuator in the proximal direction, a length of the cutting wire between the first location and the second location is decreased.

16. The method of claim 15 wherein the method does not include passing the frame in the extended state and the cutting wire, over a fundus of the uterus to locate the frame on an opposite side of the uterus from the cutting wire.

17. A method of cutting tissue, the method comprising
providing the surgical instrument as recited at claim 10,
with the frame in the retracted state and located in the lumen, passing the surgical instrument through an incision in a patient,
extending the frame from the elongate shaft distal end to place the frame in the extended state,
placing the cutting wire in contact with tissue to cut the tissue by moving the cutting wire actuator in a proximal direction, wherein, in response to moving the cutting wire actuator in the proximal direction, a length of the cutting wire between the first location and the second location is decreased.

18. The instrument of claim 1 wherein, in response to the frame being moved to the extended state, the cutting wire actuator is configured to adjust a length of the cutting wire between the first location and the second location.

19. The instrument of claim 10 wherein, in response to the frame being moved to the extended state, the cutting wire actuator is configured to adjust a length of the cutting wire between the first location and the second location.

20. The instrument of claim 1 wherein the frame includes a memory shape material.

21. The instrument of claim 10 wherein the frame includes a memory shape material.

* * * * *